United States Patent [19]

Bartley et al.

[11] 4,244,889

[45] Jan. 13, 1981

[54] PRODUCTION OF ACETAMIDES WITH RHODIUM-MANGANESE CATALYSTS

[75] Inventors: William J. Bartley; George L. O'Connor, both of Charleston, W. Va.

[73] Assignee: Union Carbide Corporation, New York, N.Y.

[21] Appl. No.: 105,244

[22] Filed: Dec. 19, 1979

[51] Int. Cl.³ .......................................... C07C 102/00
[52] U.S. Cl. .................................... 564/132; 252/460
[58] Field of Search ...................... 260/561 R; 252/460

[56] References Cited

U.S. PATENT DOCUMENTS

| | | | |
|---|---|---|---|
| 1,532,428 | 4/1925 | Meyer et al. | 260/561 R |
| 1,787,483 | 1/1931 | Lacy | 260/561 R |
| 2,204,371 | 6/1940 | Loder | 260/561 R |
| 2,422,632 | 6/1947 | Olin et al. | 260/561 R |
| 2,677,706 | 5/1954 | Giachino | 260/561 R |
| 3,530,182 | 9/1970 | Haynes et al. | 260/561 R |
| 3,726,926 | 4/1973 | Brown et al. | 260/585 R |
| 3,917,661 | 11/1975 | Pruett et al. | 260/561 R |
| 4,014,913 | 3/1977 | Ellgen et al. | 260/449 R |

FOREIGN PATENT DOCUMENTS

| | | |
|---|---|---|
| 371555 | 4/1932 | United Kingdom . |
| 397852 | 8/1933 | United Kingdom . |
| 718759 | 11/1954 | United Kingdom . |

*Primary Examiner*—Arthur P. Demers
*Attorney, Agent, or Firm*—Bernard Lieberman

[57] ABSTRACT

A heterogeneous process for selectively producing acetamides in which the acyl nitrogen is otherwise bonded to methyl, ethyl, hydrogen or combinations thereof which comprises contacting a mixture of carbon monoxide, hydrogen and a nitrogen-containing compound selected from the group consisting of ammonia, nitric oxide and mixtures thereof with a heterogeneous solid catalyst comprising rhodium and manganese. The acetamides of the invention are formed in a collective amount of at least 25 weight percent of the total amide products of the reaction.

6 Claims, No Drawings

PRODUCTION OF ACETAMIDES WITH RHODIUM-MANGANESE CATALYSTS

This invention relates to a method of preparing acetamides in which the acyl nitrogen is otherwise bonded to methyl, ethyl, hydrogen, or combinations thereof. More particularly, the invention relates to the preparation of such acetamides by the reaction of a synthesis gas with ammonia and/or nitric oxide in the presence of a rhodium-manganese catalyst.

The production of amides by the reaction of ammonia and/or an amine with various combinations of reactants, such as, carbon monoxide, hydrogen, olefins and alcohols is extensively described in the prior art. Thus, for example, U.S. Pat. Nos. 1,532,428 and 1,787,483 describe the formation of formamide by the reaction of carbon monoxide and ammonia; U.S. Pat. No. 2,204,371 discloses the production of substituted formamides by the catalytic reaction of an alcohol, carbon monoxide and ammonia; U.S. Pat. No. 2,422,632 discloses the production of aliphatic amides by the reaction of an olefin, carbon monoxide and either ammonia or an amine; and U.S. Pat. No. 3,530,182 is directed to the catalytic production of alkyl or aryl formamides by the reaction of carbon dioxide, hydrogen and an amine. The processes of these patents, in common with most amide synthesis processes disclosed in the art, are generally characterized by the predominant formation of formamide and substituted formamides among the amide products of the reaction. The present invention is directed to the selective production of acetamide and/or methyl and ethyl substituted acetamides which heretofore have not been produced in appreciable quantities directly from a synthesis gas reaction. The present invention is predicated on the discovery that a catalyst containing rhodium and manganese can selectively produce such acetamides to the substantial exclusion of other amide products.

The formation of acetamide from the reaction of synthesis gas and ammonia is disclosed in United Kingdom Pat. No. 371,555. The patent suggests the following catalysts as being useful for the reaction: pumice stone, carbon powder, copper and aluminum oxide. The examples provided in the patent do not identify the various products produced by the reaction nor the amount of acetamide produced by such reaction.

A catalyst containing rhodium and manganese in combination is known, although not for the production of amides. U.S. Pat. No. 4,014,913 to Ellgen et al discloses the use of a Rh-Mn catalyst for the selective preparation of acetic acid, acetaldehyde and ethanol from a synthesis gas mixture. However, the use of such catalyst for the production of amides has heretofore not been contemplated.

SUMMARY OF THE INVENTION

The process of the invention describes a catalyst for the selective production of acetamides in which the acyl nitrogen is otherwise bonded only to members selected from among methyl, ethyl, hydrogen and combinations thereof. The heterogeneous process involves contacting a solid catalyst comprising rhodium and manganese with a mixture comprising hydrogen, carbon monoxide and a nitrogen-containing compound selected from the group consisting of ammonia, nitric oxide and mixtures of same under suitable reaction conditions to produce the desired acetamides.

PROCESS DISCUSSION

The reaction is conducted at reaction conditions of temperature, pressure, gas composition and space velocity to produce the defined acetamides in a collective amount which is at least about 25 wt. %, and under preferred reaction conditions at least 50 wt. %, of the total amide products formed by the reaction.

Conditions of temperature, of pressure, and of gas composition are usually within the ranges that are essentially conventional for synthesis gas conversions such as those employed in the production of methanol. Thus, existing technology and equipment may generally be used to effect the reaction.

The reaction is highly exothermic, with both the thermodynamic equilibrium and the kinetic reaction rates being governed by the reaction temperature. Average catalyst bed temperatures are usually within the range of about 200°–450° C., but for optimum conversions, bed temperatures are kept within the range of about 250°–450° C., typically about 250°–350° C.

The reaction temperature is an important process variable, affecting not only total productivity but selectivity toward the desired amide products. Over relatively narrow temperature ranges, as for example 10° C. or 20° C., an increase in temperature may somewhat increase total synthesis gas conversion, tending to increase the production of amides. At the same time, however, higher temperatures favor methane production, which apparently increases more rapidly at higher temperatures than does conversion of reactants to amide products. Thus, for a given catalyst and with all other variables held constant, the optimum temperature will depend more on product and process economics than on thermodynamic or kinetic considerations, with higher temperatures tending to increase the production of amide products but disproportionately increasing the co-production of methane.

In the discussions above, the indicated temperatures are expressed as average, or mean, reaction bed temperatures. Because of the exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example, the use of fluidized bed reaction zones, the use of multistage fixed bed adiabatic reactors with inter-stage cooling, or relatively small catalyst particles placed in tube-and-shell type reactors with a coolant fluid surrounding the catalyst-filled tubes.

The reaction zone pressure is desirably within the range of about 15 psig to about 10,000 psig, economically within the range of about 300–5,000 psig. In general, higher reaction zone pressures increase the total weight of product obtained per unit time and likewise improve the selectivity toward amide products.

The ratio of hydrogen to carbon monoxide in the synthesis gas may vary widely. Normally the mole ratio of hydrogen to carbon monoxide is within the range of 20:1 to 1:20, preferably within the range of about 5:1 to about 1:5. Increasing the ratio tends to increase the total rate of reaction sometimes quite significantly, and has a smaller though favorable effect on the rate of production of amide products, but concurrently increases selectivity to methane.

The percent conversion of CO to products is an important process variable. At low conversions e.g., less than about one-fourth of the CO per pass and preferably not more than about one-eighth, the formation of the amides of the present invention is increasingly favored relative to the other products. This conversion is conveniently achieved by employing a high space velocity correlated with other reaction variables (e.g., temperature, pressure, gas composition and catalyst). Space velocities in excess of about $10^2$ gas hourly space velocity (volumes of reactant gas, at 0° C. and 760 mm mercury pressure, per volume of catalyst per hour, commonly referred to as "GHSV") are generally employed, although it is preferable that the space velocity be within the range of about $10^3$ to about $10^6$ per hour. With regard to the amide products formed, increased space velocities favor the formation of acetamide and N-monosubstituted acetamides, while decreased space velocities, i.e., below $10^4$ hr.$^{-1}$, favor the formation of N,N-disubstituted acetamides. Methyl-substituted acetamides will normally constitute only a minor fraction of the amide products formed.

The concentration of nitrogen-containing compound in the reactant gas mixture affects total productivity as well as the amide product distribution. Generally, the effect of increasing the concentration of ammonia and/or nitric oxide in the feed is to decrease the overall rate of reaction and increase the selectivity of the reaction to amides. Conversely, lower concentrations of ammonia and/or nitric oxide enhance the productivity of the reaction but disproportionately favor the production of methane, alcohols and acetic acid thereby lowering the reaction selectivity to amides. With regard to the amide products formed, at a fixed conversion of CO, increasing the concentration of ammonia and/or nitric oxide tends to favor the formation of the less substituted amides, such as, acetamide and N-ethylacetamide, while decreasing the concentration of ammonia and/or nitric oxide favors the formation of the more substituted amides.

The Rh-Mn catalyst of the invention comprises rhodium in combination with manganese upon a support material. This is typically effected by depositing rhodium and manganese onto a particulate support material and placing the supported combination into the reaction zone. On the basis of experience to date, the amount of catalyst on the support should range from about 0.01 weight percent to about 25 weight percent, based on the combined weight of the metals and the support material. Preferably, the amount of catalyst is within the range of from about 0.1 to about 10 weight percent.

A relatively high surface area particulate support, e.g., one having a surface area upwards of about 1.0 square meters per gram (BET low temperature nitrogen adsorption isotherm method), is preferred, desirably upwards of about 10 square meters per gram, although surface area alone is not the sole determinative variable. Based on research to date, silica gel and titania are preferred as the catalyst base or support, with graphite, graphitized carbon, alpha alumina, zirconia, magnesia, eta-alumina, gamma-alumina, and active carbon being less desirable.

For the purpose of this invention, rhodium deposited on either particles of manganese oxide or a carrier containing manganese is substantially the same as rhodium and manganese codepodited on any of the above support materials.

The rhodium and manganese may be deposited onto the catalyst base or support by any of the techniques commonly used for catalyst preparation, as for example, impregnation from an organic or inorganic solution, precipitation, coprecipitation, or cation exchange. Conveniently, a solution of a heat decomposable inorganic or organic rhodium compound and manganese compound is appropriately contacted with the support material, and the support then dried and heated, the latter advantageously under reducing conditions, to form the finely dispersed manganese-containing rhodium catalyst. Any of these materials may be deposited concurrently or sequentially.

The rhodium deposited is typically in metal form, desirably as fine discrete particles. The form of the manganese component is, however, not completely appreciated. It may be chemically associated with the rhodium or it may be in a physical admixture with the rhodium. For example, the manganese may be alloyed with the rhodium or not, in the form of a metal or an oxidized state of the metal, or it may be in the form of an oxide, a silicate, an aluminate, a carbonate, or the like.

DESCRIPTION OF TEST REACTOR

The reactor used in these studies was a 316 stainless steel, bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on Mar. 16-20, 1969, and obtainable from AIChE at 345 East 47th St., New York, N.Y. 10017. The autoclave was internally gold plated and the interior volume was about 1 liter. A variable speed, magnetically drive fan continuously recirculated the reaction mixture over the catalyst bed. The following modifications were found to facilitate operation and inhibit run-away methanation reactions:

1. Hydrogen feed gas was introduced continuously at the bottom of the autoclave through the well for the shaft of the Magnedrive agitator.

2. Carbon monoxide feed gas was introduced continuously through a separate port at the bottom of the autoclave, in order to avoid a hydrogen-rich zone in the autoclave.

Effluent gases were removed through a port in the side of the reactor. Condensable liquid products were removed from the exit stream in a brine-cooled condenser at ca. 5° to 10° C. and were collected in a holding tank under pressure. After venting to atmospheric pressure, the non-condensable components were samples through a rubber septum for analysis. The exit stream was then sent through a wet-test meter to determine its total volume. No external recycle was employed.

DESCRIPTION OF THE TEST PROCEDURE

The bulk volume of the weighed catalyst sample was determined and the sample was placed in the catalyst basket. The quantity of catalyst charged was chosen to provide an estimated reaction gas conversion of less than 10 percent. Gold-plated screens and thin layers of glass wool were placed above and below the catalyst bed to prevent circulation of solid fines. The catalyst basket was charged to the reactor, and the reactor then sealed. The sealed reactor and the process lines were pressure tested at ambient temperatures and 1,000 psig using a nitrogen, hydrogen, or a mixture of the two.

When the reactor was shown to be leak free, pure hydrogen was passed through the reactor at 1,000 psig and the temperature raised to about 250° C. The hydrogen and carbon monoxide flows were then adjusted at a mole ratio of 1:1 to give an approximate purge rate of 450 STP* liters/hr. corresponding to a space velocity of about 9,000 STP volumes of gas per volume of catalyst per hour. The $H_2/CO$ ratio was determined by gas chromatographic analysis of an effluent gas aliquot.

*STP refers to standard temperature and pressure defined at 0° C. and 1 atmosphere pressure.

When the desired gas composition was obtained, the reactor temperature was raised to 300° C. When conditions had stabilized, concentrated ammonia was pumped (as a liquid) to the reactor at a rate of about 13 ml./hr. using an Altex Scientific Inc. Model 100 piston pump (Table I) or nitric oxide was introduced to the reactor to provide a 1% concentration in the reaction gas (Table II). A period of about one hour was allowed for the reactor to reach a steady state at the new operating conditions before beginning to measure actual time of reaction. A sample of liquid product was collected over a one-hour period by cooling the product-containing gas in a brine-chilled condenser at 1,000 psig and then collecting the liquid product in a one-liter stainless steel receiver. The liquid sample was then analyzed by gas chromatography. The non-condensable gases were metered through a wet-test meter to determine their volume, and a gas sample was collected and analyzed by gas chromatography to determine its composition. The combined results are reported in Table I below.

CATALYST PREPARATION

The catalyst cited in Table I below was prepared as follows:

Rhodium trichloride and manganese nitrate were dissolved in one pore volume of distilled water at ambient temperature. Davison Grade 59 Silica Gel (8–20 mesh) was placed in a vacuum flask. The top of the flask was sealed with a rubber septum, and the flask was evacuated through the side arm. A syringe needle was then used to inject the rhodium and iron solution onto the evacuated support while shaking the flask. When addition was complete, the impregnated support was allowed to stand at one atmosphere for ca. 30 minutes. It was then dried in a nitrogen atmosphere as follows: 85° C. (1 hr.); 110° C. (2 hrs.); 150° C. (2 hrs.); 300° C. (2 hrs.). The dried, impregnated support was placed in a quartz tube through which hydrogen was continuously passed. The temperature was raised to 500° C. over a 5-hour period and held at that value for 1 hour. The reduced catalyst was then cooled to ambient temperature in an atmosphere of flowing hydrogen.

In order to remove significant amounts of impurities which were present in the support material as received from the manufacturer, the Davison TM Grade 59 silica support was initially "washed" with oxalic acid prior to being used as the catalyst support. Such treatment consisted of passing a mixture of oxalic acid, glycerine, and water in proportions of 1:1.5:2.5 by weight, respectively, through a bed of support material (length/diameter ratio of about 20 to 25) contained within a glass tube which drained through a stopcock at its base. The contents of the tube were maintained at about 90° C. by means of resistance heating wire wrapped around the exterior of the tube. About 2.5 volumes of oxalic acid solution were used to wash one volume of 8–20 mesh silica gel over a three-hour period. The material was then washed with about six volumes of distilled water at 90° C. over a period of about four hours and then dried at 350° C. for about four hours.

The chemical analysis of the silica gel for iron, aluminum, sodium and calcium impurities following the above-described treatment was as follows:

Iron as $Fe_2O_3$: 0.01%±0.004%
Aluminum as $Al_2O_3$: 0.01%±0.004%
Sodium as $Na_2O$: 0.01%±0.004%
Calcium as $CaO$: 0.02%±0.01%

Tables I and II which follow provide the rate of product formation and the reaction carbon efficiency to products for the above-described rhodium-manganese catalyst. As noted from the Tables, the amide product mixture was predominately comprised of acetamides in accordance with the invention.

TABLE I

PERFORMANCE DATA[a] FOR SUPPORTED RHODIUM-MANGANESE CATALYST[b] USING AN AMMONIA-SYNTHESIS GAS FEED MIXTURE

| Component | Rate[c] | Carbon Efficiency (%)[d] |
|---|---|---|
| Methanol | .014 | 0.3 |
| Ethanol | .071 | 2.4 |
| Acetic Acid | .34 | 8.8 |
| N,N-Diethylformamide | .19 | 7.3 |
| N,N-Diethylacetamide | .37 | 15.0 |
| N-Ethylacetamide | .38 | 13.6 |
| Butyramide | .24 | 8.6 |
| Methane | .78 | 37.9 |
| $C_2$-Hydrocarbons[e] | .06 | 3.7 |
| $C_3$-Hydrocarbons[f] | .04 | 2.2 |

[a]Test conditions comprised a temperature of 300° C., a reaction pressure of 1000 psig, a 1:1 mole ratio of $H_2/CO$, a feed rate of conc. $NH_4OH$ of 13 ml/hr and a gas space velocity of 18,000 $hr^{-1}$.
[b]The catalyst comprised 2.5 weight percent rhodium and 0.25 weight percent manganese supported on Davison TM Grade 59 silica gel. The catalyst volume was 25 cc.
[c]"Rate" is the rate of synthesis of the indicated product in pounds per product per cubic foot of catalyst per hour (lb/cf/hr).
[d]Percent carbon efficiency to a particular product is defined as 100 times the number of moles of carbon in that product divided by the number of moles of CO converted to products other than $CO_2$.
[e]Represents combined ethane and ethylene.
[f]Represents combined propane and propene.

TABLE II

PERFORMANCE DATA[a] FOR SUPPORTED RHODIUM-MANGANESE CATALYST[b] USING A NITRIC OXIDE-SYNTHESIS GAS FEED MIXTURE

| Component | Rate[c] | Carbon Efficiency (%)[d] |
|---|---|---|
| Ethanol | 0.24 | 1.3 |
| Acetic Acid | 4.6 | 20.0 |
| N,N-Diethylformamide | 0.1 | 0.6 |
| N,N-Diethylacetamide | 1.1 | 7.4 |
| N-Ethylacetamide | 1.7 | 10.2 |
| N-Methylacetamide | 0.4 | 2.1 |
| Butyramide | 1.9 | 11.4 |
| Methane | 4.6 | 37.6 |
| $C_2$-Hydrocarbons[e] | 0.7 | 6.5 |
| $C_3$-Hydrocarbons[f] | 0.5 | 2.9 |

[a]Test conditions comprised a temperature of 300° C., a reaction pressure of 1,000 psig, a reaction gas of 1:1 mole ratio of $H_2/CO$ containing 1% nitric oxide and a gas space velocity of 36,000 $hr^{-1}$.
[b]The catalyst comprised 2.5 weight percent rhodium and 1.0 weight percent manganese supported on Davison TM Grade 59 silica gel. The catalyst volume was 12.5 cc.
[c]"Rate" is the rate of synthesis of the indicated product in pounds per product per cubic foot of catalyst per hour (lb/cf/hr).
[d]Percent carbon efficiency to a particular product is defined as 100 times the number of moles of carbon in that product divided by the number of moles of CO converted to products other than $CO_2$.
[e]Represents combined ethane and ethylene.
[f]Represents combined propane and propene.

What is claimed is:

1. A heterogeneous process for producing acetamides in which the acyl nitrogen is otherwise bonded to methyl, ethyl, hydrogen or combinations thereof which comprises contacting a mixture of carbon monoxide, hydrogen and a nitrogen-containing compound selected from the group consisting of ammonia, nitric oxide and mixtures thereof with a heterogeneous solid catalyst comprising rhodium and manganese at reaction conditions which comprise a temperature of from about 200° to about 450° C., a pressure of from about 15 to about 10,000 psig and a mole ratio of hydrogen to carbon monoxide of from about 20:1 to about 1:20.

2. The process of claim 1 wherein said acetamides are formed in a collective amount of at least 25 weight percent of the total amide products of the reaction.

3. The process of claim 1 wherein said reaction conditions include a temperature within the range of about 250°–350° C., a pressure within the range of about 300–5000 psig and a mole ratio of hydrogen to carbon monoxide within the range of about 5:1 to 1:5.

4. The process of claim 1 wherein the conversion of CO is less than about one-fourth on a single pass basis.

5. The process of claim 1 wherein the space velocity of said mixture of hydrogen, carbon monoxide and nitrogen-containing compound is in excess of about $10^2$ GHSV.

6. The process of claim 5 wherein said space velocity is within the range of about $10^3$ to $10^6$ GHSV.

* * * * *